(12) United States Patent
Fortineau

(10) Patent No.: US 8,709,994 B2
(45) Date of Patent: Apr. 29, 2014

(54) FRAGRANCE COMPOUNDS

(75) Inventor: Anne-Dominque Fortineau, Asnières sur Seine (FR)

(73) Assignee: Givaudan Nederland Services B.V., Naarden (NL)

(*) Notice: Subject to any disclaimer, the term of this patent is extended or adjusted under 35 U.S.C. 154(b) by 26 days.

(21) Appl. No.: 12/513,311

(22) PCT Filed: Oct. 18, 2007

(86) PCT No.: PCT/GB2007/003961
§ 371 (c)(1),
(2), (4) Date: Jun. 3, 2009

(87) PCT Pub. No.: WO2008/053148
PCT Pub. Date: May 8, 2008

(65) Prior Publication Data
US 2010/0069287 A1    Mar. 18, 2010

(30) Foreign Application Priority Data
Nov. 4, 2006 (GB) .................................. 0622037.0

(51) Int. Cl.
*C11B 9/00* (2006.01)

(52) U.S. Cl.
USPC .......................................................... 512/22

(58) Field of Classification Search
USPC ........................................ 512/1, 22; 568/420
See application file for complete search history.

(56) References Cited

U.S. PATENT DOCUMENTS

2003/0148919 A1* 8/2003 Markert et al. ................. 512/22

FOREIGN PATENT DOCUMENTS

| EP | 1054053 A2 * | 11/2000 | ............... C11B 9/00 |
| JP | 48035065 | * 10/1973 | ............. C07C 47/28 |
| JP | 07-330653 A | 12/1995 | |

OTHER PUBLICATIONS

Ohloff et al Helvetica Chimica acta pp. 1343-1354.pdf., 1983, Jul. 23, 2013.*
Japanese Office Action for JP 2009-535109 dated Jan. 15, 2013.

* cited by examiner

*Primary Examiner* — Ling Choi
*Assistant Examiner* — Lanee Reuther
(74) *Attorney, Agent, or Firm* — Norris McLaughlin & Marcus PA

(57) ABSTRACT

A compound having the structure (A) where R1 is C1 to C5 alkyl, and R2 to R5 are independently selected from H and methyl, having a strong odor and for use as a perfumery ingredient, particularly in Muguet accords/fragrances, is provided.

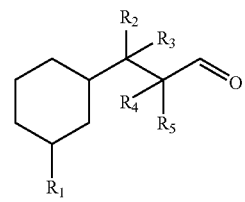

(I)

15 Claims, No Drawings

FRAGRANCE COMPOUNDS

This is an application filed under 35 USC 371 of PCT/GB2007/003961.

FIELD OF THE INVENTION

The invention relates to the discovery of novel fragrance compounds, and perfumes and perfumed products comprising the novel compounds.

BACKGROUND

A major area of interest in the fragrance industry is to find high odour impact fragrance materials which can provide superior performance at lower concentrations giving cost savings and lower environmental impact.

Muguet (Lily of the Valley) is an important area in perfumery (M Boelens and H Wobben, Perfumer & Flavorist, 1980, 5 (6), 1-8) and the odour is created by a combination of fragrance ingredients, of which 3-(3/4-alkylphenyl)propanals such as Bourgeonal™ (3-(4-tert-butylphenyl)propanal, U.S. Pat. No. 2,976,321), Florhydral™ (3-(3-isopropylphenyl)butanal, EP 368156), Lily Aldehyde™ (3-4-tert-butylphenyl)-2-methylpropanal, U.S. Pat. No. 2,875,131) and Cyclamen Aldehyde™ (3-(4-isopropylphenyl)-2-methylpropanal, U.S. Pat. No. 1,844,013) provide floral, green and in particular watery aspects. All of these materials are used in Muguet accords in high volumes to good effect.

The relationship between molecular structure and odour has intrigued and perplexed scientists for two and a half millennia since Democritus and Epicurus first postulated a causal relationship among philosophical circles in Athens. The ability to accurately and consistently predict the odour of putative molecules from their molecular structure continues to prove elusive. Recent developments (which led to the award of a Nobel Prize) in molecular biology have now given an insight into the reasons behind this. Discovery of the gene family encoding for olfactory receptor proteins (L. B. Buck and R. Axel, *Cell*, 1991, 65, 175-187) paved the way for confirmation that the sense of smell is combinatorial in nature and uses an array of hundreds of different receptor types. (B. Malnic, J. Hirono, T. Sato and L. B. Buck, *Cell*, 1999, 96, 713-723) Some of the issues raised by this in terms of odorant design are described by no less a figure than another Nobel Laureate E. J. Corey in a paper on the understanding of odorant-receptor interaction. (S. Hong and E. J. Corey, *J. Amer. Chem. Soc.*, 2006, 128, 1346-1352). A review on the subject shows that, far from making rational odorant design easier, this new understanding indicates that accurate and consistent prediction of odour properties will remain beyond our grasp for the foreseeable future. (C. S. Sell, *Angew. Chem. Int. Edn.*, 2006, 45, 6254-6261) Furthermore, an essay on property prediction from molecular structure (M. Jansen and J. C. Schoen, *Angew. Chem. Int. Edn.*, 2006, 45, 3406-3412) suggests that, at an even deeper level, all chemical properties of a proposed structure are not accurately and consistently predictable.

In a study made by R Pelzer et al (R Pelzer, U Harder, A Krempel, H Sommer, S Surburg and P Hoever in Recent Developments in Flavour & Fragrance Chemistry Proceedings of the 3rd International Haarmann & Reimer Symposium, Ed R Hopp and K Mori, VCH, 1993 pp 29-67), 181 substances possessing different aspects of the Lily of the Valley fragrance were investigated with the use of computer models. For the aldehydic materials, 41 in total, the generic fragment structure

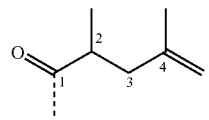

was developed and it was stated, amongst other requirements, that "a double bond at C-4 is particularly advantageous, and may also be part of an aromatic system".

There are a smaller number of aldehydic materials that are non-aromatic and possess Muguet-like odours but these tend to have alicyclic terpinoid-like structures such as Trimenal.

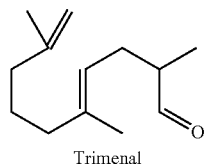

Trimenal

EP 1054053 A discloses non-aromatic aldehydes with the generic structure of:

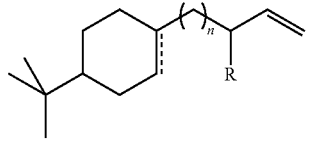

where R=H or Me, the dotted line representing either a double or single bond and n=0 (when dotted line represents a single bond) and 1 (when the dotted line represents a double bond). In the latter case, the material was described as having an aldehydic, flowery-lily of the valley, fatty type of odour with a Lily Aldehyde™/Bourgeonal™ connotation but is described as definitely more floral, more white flower than that of Lily Aldehyde™. This molecule also fits the Pelzer model in that unsaturation is present at the C-4 position.

3-(3-methylcyclohexyl)propanal is disclosed in "Sur l'addition radiculaire d'acide bromhydrique, sur quelques composés allyliques cycloniques en présence de peroxyde de diterbutyle. Réactions de substitution sur les bromures", J-M Pabiot and R Pallaud, C. R. Acad. Sc. (1971), 273(6), 475-7. However no odour properties are disclosed.

SUMMARY OF THE INVENTION

Surprisingly we have found that 3-(3-alkylcyclohexyl)propanals provide a higher odour impact relative to the commercially available substituted 3-(3/4-alkylphenyl)propanals. This result is unexpected, since it is commonly known that Muguet (Lily of the Valley) odorants based on aldehydic functionality have defined structural requirements, in particular, unsaturation in the six-membered ring.

Thus, in a first aspect, the invention provides a compound having the structure

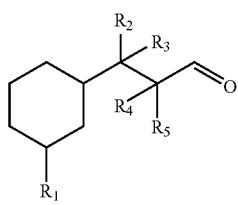

(Formula 1)

where $R_1$ is $C_1$ to $C_5$ alkyl and $R_2$ to $R_5$ are independently selected from H and methyl, with the proviso that when $R_2$ to $R_5$ are each H then $R_1$ is not methyl.

In a second aspect, the invention provides a perfume comprising the compound of Formula 1 where $R_1$ is $C_1$ to $C_5$ alkyl, and $R_2$ to $R_5$ are independently selected from H and methyl.

In a third aspect, the invention provides use of a compound of Formula 1 where $R_1$ is $C_1$ to $C_5$ alkyl, and $R_2$ to $R_5$ are independently selected from H and methyl, for use as a perfumery ingredient.

Such novel aldehyde compounds have been surprisingly found to have a strong and pleasant odour and are suitable for use as perfume ingredients, particularly in Muguet accords/fragrances.

Preferably $R_1$ is selected from isopropyl, tert-butyl, sec-butyl, iso-butyl, 2,2-dimethylpropyl.

Preferred materials are where at least one of $R_2$ and $R_3$ is H and at least one of $R_4$ and $R_5$ is H. A particularly preferred compound is where $R_1$ is tert-butyl and $R_2$ to $R_5$ are each H.

The odour properties of the aldehydes of the invention mean that an aldehyde, (including corresponding acetals or Schiffs bases), or mixture of aldehydes in accordance with the invention, may be used as such to impart, strengthen or improve the odour of a wide variety of products, or may be used as a component of a perfume (or fragrance composition) to contribute its odour character to the overall odour of such perfume.

For the purposes of this invention a perfume means a mixture of fragrance materials, if desired mixed with or dissolved in a suitable solvent or mixed with a solid substrate.

The quantities in which one or more aldehydes according to the invention can be used in perfumes may vary within wide limits and depend, inter alia, on the nature and the quantity of the other components of the perfume in which the aldehyde is used and on the olfactive effect desired. It is therefore only possible to specify wide limits, which, however, provide sufficient information for the specialist in the art to be able to use an aldehyde according to the invention for his specific purpose. Typically, a perfume comprises one or more aldehydes in accordance with the invention in an olfactively effective amount. In perfumes an amount of 0.01% by weight or more of an aldehyde according to the invention will generally have a clearly perceptible olfactive effect. Preferably the amount is from 0.1 to 80% by weight, more preferably at least 1% by weight.

In a further aspect, the invention provides a perfumed product comprising a novel compound or perfume disclosed herein.

Example of such products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, pre-shave, aftershave, skin and other lotions, talcum powers, body deodorants and antiperspirants, etc.

The amount of the aldehyde according to the invention present in products will generally be at least 10 ppm by weight, preferably at least 100 ppm, more preferably at least 1000 ppm. However, levels of up to about 20% by weight may be used in particular cases, depending on the product to be perfumed.

It has also been surprisingly discovered that certain aldehydes in accordance with the invention show good substantivity to hair and cloth, both wet and dry, and hence have good potential for use in fabric treatment products and hair care products.

It has also been surprisingly discovered that aldehydes in accordance with the invention have antibacterial and antimicrobial properties, rendering them particularly suitable for inclusion in products as described above. In particular 3-(3-tert-butylcyclohexyl)propanal has been found to have excellent activity against *Staphylococcus aureus*. In addition, isomers of this material (e.g. 3-(3-isopropylcyclohexyl)butanal) have also been found to have excellent activity against *Staphylococcus aureus*, and may have some use in antibacterial fragrance technology in some applications.

A further surprising property of certain aldehydes of the present invention is the ability to possess insect repellency properties. In particular it has been found that 3-(3-tert-butylcyclohexyl)propanal has excellent repellency properties against mosquitoes and ants.

A further surprising property of certain aldehydes of the present invention is the ability to act as a malodour counteractant. In particular, 2-methyl-3-(3-methylcyclohexyl)propanal, 3-(3-methylcyclohexyl)propanal and 3-(3-tert-butylcyclohexyl)propanal were found to be particularly good malodour counteractants, especially against bathroom malodour.

Preparation

The compounds according to the invention may be prepared according to procedures known in the art. The 3-(3-alkylcyclohexyl)propanals may be prepared in two stages from the corresponding 3-(3-alkylphenyl)propanals. Firstly, the phenyl ring may be hydrogenated using catalytic techniques typically used for hydrogenation of substituted benzene (R L Augustine in Heterogeneous Catalysis for the Synthetic Chemist, 1996, Marcel Dekker Inc., New York, ISBN 0-8247-9021-9, pp 403-437). This hydrogenation technique will typically also hydrogenate the aldehyde function of 3-(3-alkylphenyl)propanals and thus the product produced will be 3-(3-alkylcyclohexyl)propan-1-ols. Therefore secondly, the resultant alcohols are typically oxidised back to the aldehyde using stoichiometric oxidants such as 1,1,1-Tris(acetyloxy)-1,1-dihydro-1,2-benziodoxol-2-(1H)-one (Dess-Martin periodinane) or catalytic vapour phase dehydrogenation using catalysts such as copper chromite at 200-250° C., under 30 mBar.

Alternatively the 3-(3-alkylcyclohexyl)propanals may be prepared in three stages from the corresponding 3-(3-alkylphenyl)propanals via acetalisation. Firstly, the aldehyde function is converted to an acetal by reaction with an alcohol or suitable diol according to procedures known in the art. A generic example of a resultant acetal from ethylene glycol is

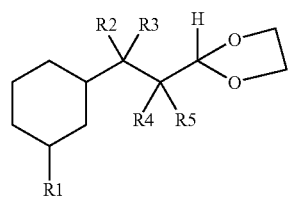

Secondly, the phenyl ring may be hydrogenated using catalytic techniques typically used for hydrogenation of substituted benzene to yield the acetal of 3-(3-alkylcyclohexy)propanal Thirdly, the acetal is hydrolysed using procedures known in the art (S Sen et al J. Org. Chem. 1997, 62, 6684-86) to obtain the target 3-(3-alkylcyclohexyl)propanal.

The 3-(3-alkylcyclohexyl)propanals according to the invention are generally obtained as mixtures of cis and trans isomers ($R_1$ and the propanal side chain are on the same side or opposite side of the cyclohexyl ring respectively). This cis/trans ratio is dependent upon the synthesis procedure used and more particularly, dependent upon the hydrogenation procedure. Generally, the odours of both isomers are different and the isomers may be separated by procedures known in the art such as column chromatography, fractional distillation and gas chromatography. The isomers may be used separately as fragrance materials or the isomer mixture obtained from the synthetic procedure may be used as such, depending on which particular odour character or mixture of odour characters is preferred for a particular application.

Also, the 3-(3-alkylcyclohexyl)propanals according to the invention exist in various stereoisomeric forms. They are obtained by the synthetic procedures described above as racemic mixtures, which may be separated into the various stereoisomers by procedures known in the art, particularly by gas chromatography using chiral columns. Therefore, the invention provides the 3-(3-alkylcyclohexyl)propanals as cis/trans and stereoisomeric mixtures as well as the various cis and trans and stereoisomers separately and includes the use of these separate isomers as fragrance materials.

Other Fragrance Materials

Other fragrance materials which can be advantageously combined with one or more aldehydes according to the invention in a perfume are, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitriles, etc., including saturated and unsaturated compounds, aliphatic, carbocyclic, and heterocyclic compounds.

Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960), "Flavor and Fragrance Materials—1991"\ Allured Publishing Co. Wheaton, Ill. USA and in H Surburg and J Panten, "Common Fragrance and Flavor Materials", Wiley-VCH, Weinheim, 2006 ISBN-13: 978-3-527-31315-0, ISBN-10: 3-527-31315-X.

Examples of fragrance materials which can be used in combination with one or more aldehydes according to the invention are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenyl-ethanol, 2phenylethyl acetate, benzyl alcohol, benzyl acetate, benzyl salicylate, styrallyl acetate, benzyl benzoate, amyl salicylate, dimethylbenzyl-carbinyl acetate, trichloromethylphenyl-carbinyl acetate, p-tert-butylcyclohexyl acetate, isononyl acetate, vetiveryl acetate, vetiverol, ahexylcinnamaldehyde, 2-methyl-3-(p-tert-butylphenyl)propanal, 2-methyl-3-(p-isopropylphenyl)propanal, 2-(p-tert-butylphenyl)-propanal, 2,4-dimethyl-cyclohex-3-enylcarboxaldehyde, tricyclodecenyl acetate, tricyclodecenyl propionate, 4-(4-hydroxy-4methylpentyl)-3-cyclohexenecarboxyaldehyde, 4-(4-methyl-3-pentenyl)-3-cyclohexenecarboxaldehyde, 4-acetoxy-3-pentyltetrahydropyran, 3-carboxy methyl-2-pentylcyclopentanone, 2-n-heptylcyclopentanone, 3-methyl-2-pentyl-2-cyclopentenone, n-decanal, n-dodecanal, 9-decenol-1, phenoxyethyl isobutyrate, phenylacetaldehyde dimethylacetal, phenylacetaldehyde diethyl acetal, geranyl nitrile, citronellyl nitrile, cedryl acetate, 3 isocamphylcyclohexanol, cedryl methyl ether, isolongifolanone, aubepine nitrile, anisic aldehyde, heliotropin, coumarin, eugenol, vanillin, diphenyl oxide, hydroxycitronellal, ionones, methylionones, isomethylionones, irones, cis-3-hexenol and esters thereof, indane musks, tetralin musks, isochroman musks, macrocyclic ketones, macrocyclic lactone musks, ethylene brassylate.

Solvents which can be used for perfumes which contain an aldehyde according to the invention are, for example: ethanol, isopropanol, diethyleneglycol mono ethyl ether, dipropylene glycol, diethyl phthalate, triethyl citrate, isopropyl myristate, etc.

The invention will be further described, by way of illustration in the following examples.

EXAMPLE 1

Preparation of 3-(3-methylcyclohexyl)propanal i) 3-(3-methylcyclohexyl)propan-1-ol

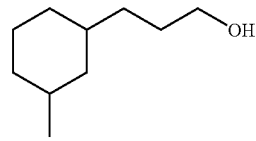

5% $Ru/Al_2O_3$ (3 g, 5 wt %), (2E)-3-(3-methylphenyl) acrylic acid (60 g, 0.37 mol) and acetic acid (300 mL) were charged into a 500 mL autoclave vessel. The mixture was vigorously stirred under a hydrogen atmosphere (40 bar) at 150° C., for 3 days. The catalyst was filtered and the product was dissolved in ethyl acetate (500 mL), washed with water (500 mL) and brine (500 mL). The organic phase was dried over sodium sulphate, filtered and evaporated to yield crude 3-(3-methylcyclohexyl)propanoic acid (60 g, 0.35 mol, 95% yield) as a colourless oil.

$LiAlH_4$ (16 g, 0.42 mol, 1.2 eq) and diethyl ether (450 mL) were charged into a 2 L three-necked round-bottom flask equipped with a mechanical stirrer and a reflux condenser and cooled at 0° C. The crude 3-(3-methylcyclohexyl)propanoic acid (60 g, 0.35 mol) was dissolved in diethyl ether (400 mL) and added dropwise to the reaction flask. The reaction mixture was then stirred for 3 h at ambient temperature. The excess of lithium aluminium hydride was hydrolyzed with saturated aqueous sodium sulphate and the mixture filtered. THF (1 L) was added to the residue and the suspension was heated to 35° C. for 1 h. The suspension was filtered and the combined organic layers were dried over sodium sulphate and evaporated to yield the crude product as an oil. Chromatography on a silica gel column with 8% EtOAc in hexane as elution agent, followed by a bulb-to-bulb distillation (0.1 mBar, 140° C.) gave pure 3-(3-methylcyclohexyl)propan-1-ol (35 g, gc purity>98%; yield=61%).

Odour: aldehydic, watery, fatty, citrus, nitrile.

Analytical Data (Predominantly One Isomer):

$^1$H NMR (400 MHz, CHLOROFORM-d) ppm: 0.46-1.72 (m, 15H); 0.85 (d, 3H); 3.57-3.64 (m, 2H).

$^{13}$C NMR (101 MHz, CHLOROFORM-d) ppm: 22.93 (q, 1C); 26.29 (t, 1C); 30.12 (t, 1C); 32.67 (d, 1C); 32.92 (t, 1C); 33.49 (t, 1C); 35.31 (t, 1C); 37.49 (d, 1C); 42.28 (t, 1C); 63.38 (t, 1C).

MS: m/z (relative intensity): 156 (M+, <1), 138 (5), 123 (5), 110 (44), 97 (46), 96 (27), 95 (100), 82 (52), 81 (42), 69 (15), 67 (23), 55 (84), 41 (23).

ii) 3-(3-methylcyclohexyl)propanal

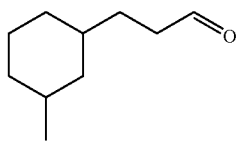

In a 2 L three-necked round-bottom flask equipped with a mechanical stirrer and a reflux condenser were introduced a solution of 3-(3-methylcyclohexyl)propan-1-ol (23.3 g, 0.15 mol) in dichloromethane (140 mL), a solution of potassium bromide (1.77 g, 15 mmol, 0.1 eq) in water (25 mL) and 2,2,6,6-tetramethyl-1-piperidinyloxy (TEMPO, 300 mg, 1.92 mmol, 0.01 eq). To this mixture was added 0.35M aqueous sodium hypochlorite (594 mL). The mixture was stirred for 3 days at 35° C. then extracted with dichloromethane (500 mL). The organic layer was washed with water (300 mL), 1N HCl (300 mL) and brine (300 mL), dried over sodium sulphate and concentrated. The crude product was chromatographed on silica gel with 8% EtOAc in hexane as elution agent, followed by a bulb-to-bulb distillation (0.01 mBar, 79° C.) to give pure 3-(3-methylcyclohexyl)propanal (11.8 g, gc purity>98%; yield=51%).

Odour: aldehydic, fatty, nitrile.

Analytical Data (Predominantly One Isomer):

$^1$H NMR (400 MHz, CHLOROFORM-d) ppm: 0.45-1.75 (m, 12H); 0.84 (d, 3H); 2.38-2.44 (m, 2H); 9.73 (t, 1H).

$^{13}$C NMR (101 MHz, CHLOROFORM-d) ppm: 22.81 (q, 1C); 26.08 (t, 1C); 29.40 (t, 1C); 32.53 (d, 1C); 32.57 (t, 1C); 35.08 (t, 1C); 37.16 (d, 1C); 41.48 (t, 1C); 41.86 (t, 1C); 203.03 (d, 1C).

MS: m/z (relative intensity): 154 (M+, <1), 136 (12), 121 (15), 110 (28), 108 (39), 97 (27), 95 (100), 82 (72), 81 (39), 69 (19), 68 (20), 67 (27), 55 (86), 41 (33).

EXAMPLE 2

Preparation of 3-(3-tert-butylcyclohexyl)propanal i) 1-(1-bromoethyl)-3-tert-butylbenzene

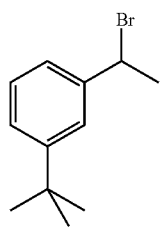

A solution of 1-tert-butyl-3-ethylbenzene (90 g, 0.54 mol) in carbon tetrachloride (600 mL) was charged into a 2 L three-necked round-bottom flask, equipped with a mechanical stirrer and a reflux condenser. The reaction was stirred vigorously while N-bromosuccinimide (97.6 g, 0.54 mol, 1 eq) was added, followed by benzoyl peroxide (0.8 g, 2.23 mmol, 0.004 eq). The reaction mixture was then heated to mild reflux for 1 h. Once cooled, the mixture was filtered and the organic phase was washed successively with water (2×300 mL), 10% Na$_2$SO$_3$ water solution (150 mL), water (2×300 mL) and a saturated NaHCO$_3$ water solution (100 mL), dried over magnesium sulphate and concentrated.

Unreacted 1-tert-butyl-3-ethylbenzene was removed by fractional distillation (8.2 mBar, 79-80° C.) to leave 1-(1-bromoethyl)-3-tert-butylbenzene (132 g, gc purity>90%; yield=95%), which was used as such for the next step.

Analytical Data:

$^1$H NMR (400 MHz, CHLOROFORM-d) ppm: 1.38 (s, 9H); 2.10 (d, 3H); 5.27 (q, 1H); 7.32-7.48 (m, 4H).

$^{13}$C NMR (101 MHz, CHLOROFORM-d) ppm: 26.97 (q, 1C); 31.29 (q, 3C); 34.70 (s, 1C); 50.25 (d, 1C); 123.79 (d, 1C); 123.81 (d, 1C); 125.41 (d, 1C); 128.35 (d, 1C); 142.81 (s, 1C); 151.47 (s, 1C).

MS: m/z (relative intensity): (no M+), 227 (2), 225 (2), 161 (100), 145 (14), 131 (10), 117 (19), 105 (12), 91 (18), 77 (10), 57 (65), 41 (20), 39 (14).

ii) 1-tert-butyl-3-vinylbenzene

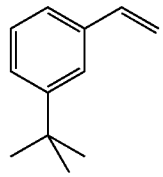

Potassium hydroxide (140.9 g, 2.51 mol, 1.9 eq), 1-(1-bromoethyl)-3-tert-butylbenzene (347.12 g, 90.9% gc pure, 1.31 mol, 1 eq) and 2-propanol (2.6 kg) were charged into a 5 L three-necked round-bottom flask, equipped with a mechanical stirrer and a reflux condenser. After stirring for 2 h at 60° C., the reaction mixture was cooled to ambient temperature and poured into ice (1.7 kg), and the product was extracted with pentane. (1.5 L). The organic phase thus obtained was washed twice with water (750 mL portions) and a saturated NaHCO$_3$ water solution (300 mL), dried over Magnesium sulphate and concentrated. The crude product was chromatographed on a silica gel column with hexane as elution agent to give the product as a colourless oil (119.6 g, gc purity of 93%), which was stabilised with 0.3 g of BHT. Flash distillation using a Vigreux column (3.4 mBar, 60-64° C.) gave 1-tert-butyl-3-vinylbenzene (105.3 g, gc purity>97%, yield=50%).

Analytical Data:

$^1$H NMR (400 MHz, CHLOROFORM-d) ppm: 1.37 (q, 9H); 5.27 (d, 1H); 5.78 (d, 1H); 6.77 (dd, 1H); 7.28-7.35 (m, 3H); 7.45 (s, 1H).

$^{13}$C NMR (101 MHz, CHLOROFORM-d) ppm: 31.31 (q, 3C); 34.62 (s, 1C); 113.42 (t, 1C); 123.17 (d, 1C); 123.42 (d, 1C); 124.92 (d, 1C); 128.23 (d, 1C); 137.22 (s, 1C); 137.35 (d, 1C); 151.30 (s, 1C).

MS: m/z (relative intensity): 160 (M+, 19), 145 (100), 128 (12), 117 (56), 115 (19), 105 (17), 91 (16), 77 (10), 63 (6), 57 (7), 51 (8), 41 (8), 39 (13).

iii) 3-(3-tert-butylphenyl)propanal

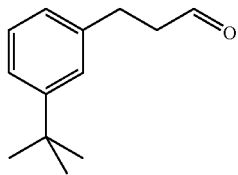

Acetylacetonatodicarbonylrhodium (I) (41 mg, 0.1 mol %) of 1-tert-butyl-3-vinylbenzene (29 g, 0.16 mol) and a solution of triphenylphosphite (261 mg, 0.99 mmol) in 88 g of toluene were added to a 250 mL autoclave vessel. The vigorously stirred reaction mixture heated for 6 h under a pressure of syn gas (mixture of hydrogen and carbon monoxide in a ratio 1:1-1 Bar), at 80° C. The crude reaction mixture was concentrated in vacuo and chromatographed on a silica gel column with 3% MTBE in hexane as elution agent to give 3-(3-tert-butylphenyl)propanal (24.5 g, gc purity>82%; yield=63%).

Odour: aldehydic, floral, rubber.

Analytical Data:

$^1$H NMR (400 MHz, CHLOROFORM-d) ppm: 1.35 (s, 9H); 2.81 (t, 2H); 2.96 (t, 2H); 7.01-7.30 (m, 4H); 9.85 (d, 1H).

$^{13}$C NMR (101 MHz, CHLOROFORM-d) ppm: 28.32 (t, 1C); 31.29 (q, 3C); 34.54 (s, 1C); 45.35 (t, 1C); 123.21 (d, 1C); 125.22 (d, 1C); 125.27 (d, 1C); 128.22 (d, 1C); 139.87 (s, 1C); 151.41 (s, 1C); 201.57 (d, 1C).

MS: m/z (relative intensity): 190 (M$^+$, 32), 175 (82), 172 (0.5), 157 (4), 147 (12), 133 (21), 131 (100), 119 (11), 117 (12), 116 (11), 115 (17), 105 (16), 91 (26), 77 (10), 65 (5), 57 (17), 41 (9).

iv) 2-[2-(3-tert-butylphenyl)ethyl]-1,3-dioxolane

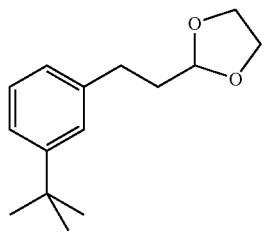 [SMILES: CC(C)(C)c1cccc(CCC2OCCO2)c1]

Ethylene glycol (15 mL, 0.27 mol, 1.2 eq), paratoluene sulfonic acid (430 mg, 1% w/w) and cyclohexane (50 mL) were charged into a 1 L three-necked round-bottom flask, equipped with a dean and stark, a reflux condenser and a mechanical stirrer. 3-(3-tert-butylphenyl)propanal (50.6 g, gc purity of 85%, 0.22 mol) was added dropwise at ambient temperature. After stirring for 2 h at reflux, the reaction mixture was cooled to ambient temperature and washed twice with water (50 mL), saturated aqueous NaHCO$_3$, dried over magnesium sulphate and concentrated to give 2-[2-(3-tert-butylphenyl)ethyl]-1,3-dioxolane in the form of a pale yellow coloured oil (60 g, gc purity>84%; yield>95%). The material was used as such for the next step.

Odour: floral, aldehydic, muguet, linalool.

Analytical Data:

$^1$H NMR (400 MHz, CHLOROFORM-d) ppm: 1.33 (s, 9H); 2.03 (m, 2H); 2.75 (m, 2H); 3.87-5.05 (m, 4H); 4.93 (t, 1H); 7.05 (m, 1H); 7.25 (m, 3H).

$^{13}$C NMR (101 MHz, CHLOROFORM-d) ppm: 30.37 (t, 1C); 31.35 (q, 3C); 34.56 (s, 1C); 35.64 (t, 1C); 64.91 (t, 2C); 103.91 (d, 1C); 122.79 (d, 1C); 125.41 (d, 2C); 128.02 (d, 1C); 141.13 (s, 1C); 151.16 (s, 1C).

MS: m/z (relative intensity): 234 (M$^+$, 7), 219 (1), 191 (3), 172 (17), 157 (12), 148 (11), 147 (13), 133 (32), 131 (24), 117 (16), 115 (16), 105 (13), 100 (40), 92 (43), 91 (22), 87 (41), 77 (6), 73 (100), 57 (48), 45 (20).

v) 2-[2-(3-tert-butylcyclohexyl)ethyl]-1,3-dioxolane

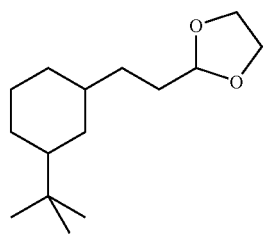 [SMILES: CC(C)(C)C1CCCC(CCC2OCCO2)C1]

5% Ru/Al$_2$O$_3$ (3 g, 5% w/w) were charged into a 100 mL autoclave vessel with 2-[2-(3-tert-butylphenyl)ethyl]-1,3-dioxolane (60 g, gc purity of 84%, 0.21 mol). The mixture was vigorously stirred under an hydrogen atmosphere (60 Bar) at 130° C. for 4 h. The reaction mixture was filtered, rinsed with cyclohexane and concentrated to give 2-[2-(3-tert-butylcyclohexyl)ethyl]-1,3-dioxolane in the form of a pale yellow coloured oil (62.1 g, gc purity>87%; yield>99%). The material was used as such for the next step.

Odour: floral, muguet, citrus, salicylate, minty.

Analytical Data (Predominantly One Isomer):

$^1$H NMR (400 MHz, CHLOROFORM-d) ppm: 0.50-1.80 (m, 14H); 0.79 (s, 9H); 3.76-3.93 (m, 4H); 4.79 (t, 1H).

$^{13}$C NMR (101 MHz, CHLOROFORM-d) ppm: 26.63 (t, 1C); 27.30 (t, 1C); 27.49 (q, 3C); 31.35 (t, 1C); 31.87 (t, 1C); 32.41 (s, 1C); 33.08 (t, 1C); 34.27 (t, 1C); 38.03 (d, 1C); 47.91 (d, 1C); 64.76 (t, 2C); 104.91 (d, 1C).

MS: m/z (relative intensity) 240 (M$^+$, <1), 239 (1), 183 (1), 163 (3), 121 (7), 95 (4), 81 (4), 79 (4), 73 (100), 67 (5), 57 (10), 45 (7), 41 (8).

vi) 3-(3-tert-butylcyclohexyl)propanal

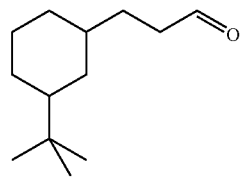

2-[2-(3-tert-butylcyclohexyl)ethyl]-1,3-dioxolane (62 g, 0.22 mol, gc purity of 87%) and dichloromethane/acetone in a 4:1 ratio (3.7 L) were charged into a 5 L three-necked round-bottom flask equipped with a reflux condenser and a mechanical stirrer. Iron (III) chloride hexahydrate (212.3 g, 0.78 mol, 3.5 eq) was added to the reaction at ambient temperature. The reaction mixture was then stirred at ambient temperature for 4 h and subsequently quenched, at 5-10° C., with the addition of a saturated aqueous NaHCO$_3$ (500 mL). The organic phase was then washed with brine (500 mL), dried over magnesium sulphate and concentrated. The resulting crude product was distilled via a Vigreux column (0.5 mBar, 82-85° C.), to give colourless oil (34.7 g, gc purity 79%). The oil was chromatographed on a silica gel column with 2% EtOAc in hexane as elution agent giving 3-(3-tert-butylcyclohexyl)propanal (17.8 g, gc purity>98%, ratio cis: trans 75:25; yield 40%).

Odour: aldehydic, floral, muguet, green.

Analytical Data (2 Isomers):

$^1$H NMR (400 MHz, CHLOROFORM-d) ppm: 0.52-0.86 (m, 3H), 0.80 (s, 9H), 0.82 (s, 9H), 0.84-1.79 (m, 21H), 2.34-2.42 (m, 2H), 2.43 (td, 2H, J=7.63, 1.83 Hz), 9.75 (t, 1H, J=1.95 Hz), 9.77 (t, 1H, J=1.83 Hz).

$^{13}$C NMR (101 MHz, CHLOROFORM-d) ppm: 21.36 (t, 1C), 23.70 (t, 1C), 26.51 (t, 1C), 27.19 (q, 3C), 27.32 (q, 3C), 27.50 (t, 1C), 27.57 (t, 1C), 29.62 (t, 1C), 29.72 (t, 1C), 30.84 (t, 1C), 32.25 (s, 1C), 32.44 (s, 1C), 32.83 (t, 1C), 33.16 (d, 1C), 34.18 (t, 1C), 37.69 (d, 1C), 41.37 (d, 1C), 41.58 (t, 1C), 42.61 (t, 1C), 47.84 (d, 1C), 203.00 (d, 1C), 203.10 (d, 1C).

Pure CIS-isomer:

Odour: aldehydic, floral, muguet, watery.

$^1$H NMR (400 MHz, CHLOROFORM-d) ppm: 0.52-0.67 (m, H); 0.76-0.86 (m, 2H); 0.82 (s, 9H); 0.94-1.02 (m, 1H); 1.12-1.25 (m, 2H); 1.47-1.57 (m, 2H); 1.65-1.79 (m, 4H); 2.43 (td, 2H, J=7.63, 1.83 Hz); 9.75 (t, 1H, J=1.95 Hz).

$^{13}$C NMR (101 MHz, CHLOROFORM-d) ppm: 26.51 (t, 1C); 27.19 (q, 3C); 27.50 (t, 1C); 29.72 (t, 1C); 32.44 (s, 1C); 32.83 (t, 1C); 34.18 (t, 1C); 37.69 (d, 1C); 41.58 (t, 1C); 47.84 (d, 1C); 203.10 (d, 1C).

MS: m/z (relative intensity) (no M$^+$), 163 (7), 152(3), 139 (29), 121 (28), 109 (3), 107 (5), 95 (26), 81 (25), 79 (20), 69 (12), 67 (23), 57 (100), 41 (41).

Pure TRANS-isomer:

Odour: aldehydic, floral, metallic.

$^1$H NMR (400 MHz, CHLOROFORM-d) ppm: 0.80 (s, 9H); 0.84-0.96 (m, 1H); 1.05-1.21 m, (2H); 1.30-1.43 (m, 2H); 1.43-1.55 (m, 2H); 1.55-1.63 (m, 1H); 1.64-1.79 (m, 4H); 2.34-2.42 (m, 2H); 9.77 (t, 1H, J=1.83 Hz).

$^{13}$C NMR (101 MHz, CHLOROFORM-d) ppm: 21.36 (t, 1C); 23.70 (t, 1C); 27.32 (q, 3C); 27.57 (t, 1C); 29.62 (t, 1C); 30.84 (t, 1C); 32.25 (s, 1C); 33.16 (d, 1C); 41.37 (d, 1C); 42.61 (t, 1C); 203.00 (d, 1C).

MS: m/z (relative intensity) (no M$^+$), 163 (4), 152 (6), 139 (34), 121 (28), 109 (5), 107 (5), 95 (30), 81 (27), 79 (22), 69 (12), 67 (24), 57 (100), 41 (45).

EXAMPLE 3

Preparation of 3-(3-methylcyclohexyl)butanal i) 3-(3-methylphenyl)butanal

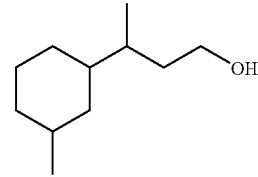

In a 1 L three-necked round-bottom flask equipped with a mechanical stirrer and a reflux condenser were introduced DMF (300 mL), 3-bromo toluene (66.3 g, 0.39 mol), of crotyl alcohol (99 mL, 1.16 mol, 3 eq), sodium carbonate (102.5 g, 0.97 mol, 2.5 eq), tetrabutyl-ammonium bromide (107.6 g, 0.39 mol, 1 eq), palladium acetate (7.8 g, 11.6 mmol, 3 mol %) and tri-o-tolyl phosphine (11.8 g, 38.7 mmol, 0.1 eq). After stirring for 1 h at 100-105° C., the reaction mixture was cooled to ambient temperature. The reaction mixture was filtered over celite. The organic phase thus obtained was diluted with MTBE (800 mL) and washed three times with water (500 mL portions), dried over magnesium sulphate and concentrated. The resulting crude product was fractionally distilled with a Vigreux column (1 mBar, 70-81° C.) to give a colourless oil (39.6 g, gc purity 90%). The oil was chromatographed on a silica gel column with 7% EtOAc in hexane as elution agent giving 3-(3-methylphenyl)butanal (12.5 g, gc purity>99%; yield 36%).

Odour: green, watery/marine, aldehydic, marenil.

Analytical Data:

$^1$H NMR (400 MHz, CHLOROFORM-d) ppm: 1.31 (d, 3H); 2.34 (s, 3H); 2.70 (m, 2H); 3.32 (m, 1H); 7.00-7.23 (m, 4H); 9.70 (t, 1H).

$^{13}$C NMR (101 MHz, CHLOROFORM-d) ppm: 21.42 (q, 1C); 22.15 (q, 1C); 34.21 (d, 1C); 51.68 (t, 1C); 123.69 (d, 1C); 127.24 (d, 1C); 127.52 (d, 1C); 128.53 (d, 1C); 138.21 (s, 1C); 145.38 (s, 1C); 201.96 (d, 1C).

MS: m/z (relative intensity) 162 (M$^+$, 71), 147 (33), 144 (13), 133 (8), 129 (14), 119 (100), 117 (37), 105 (76), 91 (61), 77 (21), 65 (16), 51 (9), 41 (13), 39 (13).

ii) 3-(3-methylcyclohexyl)butan-1-ol

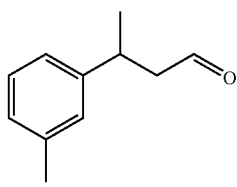

5% Ru/Al$_2$O$_3$ (500 mg, 5% w/w) was charged into a 25 mL autoclave vessel with 3-(3-methylphenyl)butanal (10 g, 61.6 mmol). The mixture was vigorously stirred under a hydrogen atmosphere (65 Bar) at 130° C. for 5.5 h. The reaction mixture was filtered, rinsed with cyclohexane and concentrated. The resulting crude product was distilled via a bulb-to-bulb distillation (4.5 mBar, 125-130° C.) to give 3-(3-methylcyclohexyl)butan-1-ol (8 g, gc purity>90%; yield 76%).

Odour: floral, muguet, green, lilac, terpineol.

Analytical Data (2 Isomers):

$^1$H NMR (400 MHz, CHLOROFORM-d) ppm: 0.60-1.95 (m, 28H); 0.80-0.86 (m, 12H); 0.82 3.56-3.70 (m, 4H).

$^{13}$C NMR (101 MHz, CHLOROFORM-d) ppm: 16.06 (q, 2C); 22.99 (q, 1C); 23.02 (q, 1C); 26.43 (t, 1C); 26.53 (t, 1C); 28.03 (t, 1C); 29.86 (t, 1C); 32.91 (d, 1C); 33.00 (d, 1C); 34.38 (d, 1C); 34.43 (d, 1C); 35.43 (t, 2C); 37.01 (t, 1C); 37.05 (t, 1C); 37.43 (t, 1C); 39.30 (t, 1C); 42.65 (d, 2C); 61.52 (t, 2C).

MS: m/z (relative intensity) (no M$^+$), 152 (3), 137 (2), 124 (57), 110 (8), 97 (77), 96 (36), 95 (51), 81 (37), 69 (21), 67 (17), 55 (100), 41 (28).

iii) 3-(3-methyl)cyclohexylbutanal

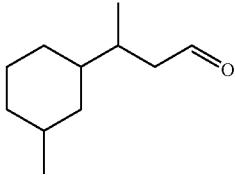

A solution of Dess Martin periodinane (17.4 g, 41 mmol, 1.1 eq) in dichloromethane (250 mL) was charged into a 2 L three-necked round-bottom flask, equipped with a mechanical stirrer and a reflux condenser. 3-(3-methylcyclohexyl)butan-1-ol (6.4 g, 38 mmol) was added dropwise, followed by a mixture of water (740 L) in dichloromethane (740 mL) at ambient temperature over 1.5 h. After stirring for 2 h at ambient temperature, the mixture was diluted with diethyl ether (200 mL) and washed with a 1:1 mixture of saturated aqueous $NaHCO_3$ and 10% $Na_2S_2O_3$ (2×100 mL) and brine (100 mL), dried over magnesium sulphate and concentrated. The oil was chromatographed on a silica gel column with 7% EtOAc in hexane as elution agent giving 3-(3-methyl)cyclohexylbutanal (1.8 g, gc purity>80%; yield 28%).

Odour: aldehydic, green, muguet.

Analytical Data (2 Isomers):

$^1$H NMR (400 MHz, CHLOROFORM-d) ppm: 0.54-0.83 (m, 4H); 0.83-0.91 (m, 12H); 1.12-1.47 (m, 8H); 1.53-1.67 (m, 6H); 1.68-1.77 (m, 2H); 1.89-1.99 (m, 2H); 2.13-2.22 (m, 2H); 2.40-2.48 (m, 2H); 9.73 (dd, 2H).

$^{13}$C NMR (101 MHz, CHLOROFORM-d) ppm: 16.87 (q, 2C); 22.92 (q, 1C); 22.93 (q, 1C); 26.25 (t, 1C); 26.32 (t, 1C); 28.57 (t, 1C); 29.68 (t, 1C); 32.78 (d, 1C); 32.87 (d, 1C); 33.00 (d, 1C); 33.02 (d, 1C); 35.21 (t, 2C); 37.91 (t, 1C); 39.01 (t, 1C); 42.55 (d, 1C); 42.56 (d, 1C); 48.50 (t, 1C); 48.51 (t, 1C); 203.46 (d, 2C).

MS: m/z (relative intensity) 168 (M$^+$, <1), 150 (2), 135 (11), 124 (75), 109 (10), 97 (49), 95 (88), 81 (21), 71 (14), 69 (18), 68 (16), 67 (17), 55 (100), 41 (33).

EXAMPLE 4

Preparation of 3-(3-isopropylcyclohexyl)butanal i) 2-[2-(3-isopropylphenyl)propyl]-1,3-dioxolane

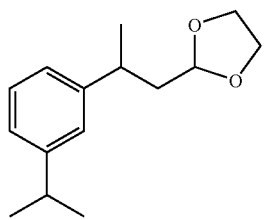 [SMILES: CC(C)c1cccc(C(C)CC2OCCO2)c1]

Ethylene glycol (18 mL, 0.32 mol, 1.2 eq), paratoluene sulfonic acid (400 mg, 1% w/w) and cyclohexane (50 mL) were charged into a 1 L three-necked round-bottom flask, equipped with a dean and stark, a reflux condenser and a mechanical stirrer. Florhydral™ 3-(3-isopropylphenyl)butanal, 49.3 g, 0.26 mol) was added dropwise at ambient temperature. The stirred mixture was then heated for 3 h at reflux. The reaction mixture was cooled at ambient temperature and washed water (2×100 mL), dried over magnesium sulphate and concentrated. The resulting crude product was distilled with a Vigreux column (7.2 mBar, 146° C.), to give 2-[2-(3-isopropylphenyl)propyl]-1,3-dioxolane (239 g, gc purity>98%; yield 97%).

Odour: floral.

Analytical Data:

$^1$H NMR (400 MHz, CHLOROFORM-d) ppm: 1.25 (d, 6H, J=7.08 Hz); 1.30 (d, 3H, J=7.08 Hz); 1.83-1.90 (m, 1H); 1.98-2.04 (m, 1H); 2.85-2.99 (m, 2H); 3.76-3.84 (m, 2H); 3.92-3.99 (m, 2H); 4.70 (dd, 1H, J=6.35, 4.15 Hz); 7.02-7.08 (m, 3H); 7.20-7.25 (m, 1H).

$^{13}$C NMR (101 MHz, CHLOROFORM-d) ppm: 22.63 (q, 1C); 24.03 (q, 2C); 34.11 (d, 1C); 36.02 (d, 1C); 42.10 (t, 1C); 64.62 (t, 1C); 64.75 (t, 1C); 103.35 (d, 1C); 124.02 (d, 1C); 124.21 (d, 1C); 125.25 (d, 1C); 128.29 (d, 1C); 146.64 (s, 1C); 148.93 (s, 1C).

MS: m/z (relative intensity) 234 (M$^+$, 1), 190 (1), 172 (7), 157 (7), 148 (43), 133 (13), 131 (13), 117 (10), 115 (12), 105 (100), 100 (1), 99 (20), 91 (22), 87 (46), 77 (8), 73 (93), 45 (22).

ii) 2-[2-(3-isopropylcyclohexyl)propyl]-1,3-dioxolane

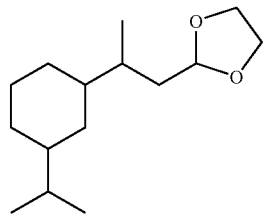 [SMILES: CC(C)C1CCCC(C(C)CC2OCCO2)C1]

5% Ru/Al$_2$O$_3$ (2 g, 5% w/w) was charged into a 100 mL autoclave vessel with 2-[2-(3-isopropylphenyl)propyl]-1,3-dioxolane (40 g, 0.17 mol). The mixture was vigorously stirred under an hydrogen atmosphere (60-65 Bar) at 130° C. for 4 h. The reaction mixture was filtered, rinsed with cyclohexane and concentrated to give 2-[2-(3-isopropylcyclohexyl)propyl]-1,3-dioxolane (126.5 g, gc purity>98%; yield>99%) in the form of a colourless oil. The material was used as such for the next step.

Odour: green, pyrazine, dusty, vetiver.

Analytical Data (2 Isomers):

$^1$H NMR (400 MHz, CHLOROFORM-d) ppm: 0.72 (dd, 2H, J=16.24, 12.08 Hz); 0.83 (d, 6H, J=6.84 Hz); 0.82 (d, 6H, J=6.84 Hz); 0.89 (d, 3H, J=6.84 Hz); 0.88 (d, 3H, J=6.84 Hz); 0.92-1.82 (m, 26H); 3.78-3.85 (m, 4H); 3.91-3.98 (m, 4H); 4.87 (dd, 2H, J=5.62, 4.64 Hz).

$^{13}$C NMR (101 MHz, CHLOROFORM-d) ppm: 16.21 (q, 1C); 16.42 (q, 1C); 19.64 (q, 1C); 19.68 (q, 1C); 19.81 (q, 1C); 19.84 (q, 1C); 26.56 (t, 1C); 26.65 (t, 1C); 28.24 (t, 1C); 29.72 (t, 1C); 29.76 (t, 1C); 29.99 (t, 1C); 31.89 (t, 1C); 33.09 (d, 1C); 33.11 (d, 1C); 33.67 (t, 1C); 34.35 (d, 1C); 34.41 (d, 1C); 38.12 (t, 1C); 38.43 (t, 1C); 43.06 (d, 1C); 43.20 (d, 1C); 44.19 (d, 1C); 44.27 (d, 1C); 64.57 (t, 1C); 64.58 (t, 1C); 64.74 (t, 1C); 64.74 (t, 1C); 104.20 (d, 1C); 104.24 (d, 1C).

MS: Major isomer: m/z (relative intensity) (no M$^+$), 152 (2), 135 (1), 109 (3), 95 (2), 82 (4), 73 (100), 69 (4), 67 (5), 55 (5), 45 (7), 41 (6).

Minor isomer: m/z (relative intensity) (no M+), 152 (2), 135 (1), 109 (3), 95 (2), 82 (4), 73 (100), 69 (4), 67 (5), 55 (5), 45 (7), 41 (7).

iii) 3-(3-isopropylcyclohexyl)butanal

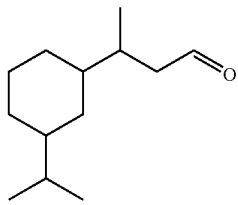

2-[2-(3-isopropylcyclohexyl)propyl]-1,3-dioxolane (5 g, 20.8 mmol) and a 4:1 mixture of dichloromethane:acetone (300 mL) were charged into a 3 L three-necked round-bottom flask equipped with a reflux condenser and a mechanical stirrer. Iron (III) chloride hexahydrate (19.7 g, 72.8 mmol, 3.5 eq) was added at ambient temperature. The reaction mixture was then stirred at ambient temperature for 4 h and subsequently quenched at 5-10° C. with the addition of saturated aqueous NaHCO₃ (500 mL). The organic phase was then washed with brine (500 mL), dried over magnesium sulphate and concentrated. The resulting crude product was distilled via a Vigreux column (1.3 mBar, 89° C.), to give 3-(3-isopropylcyclohexyl)butanal (23.9 g, gc purity>91%; yield 62%).

Odour: green, violet, orris, aldehydic.

Analytical Data (2 Isomers):
$^1$H NMR (400 MHz, CHLOROFORM-d) ppm: 0.65-0.76 (m, 2H); 0.78-0.94 (m, 4H); 0.80-0.85 (m, 6H); 0.82 (d, 6H, J=6.84 Hz); 0.90 (d, 3H, J=7.08 Hz); 0.89 (d, 3H, J=6.84 Hz); 0.97-1.10 (m, 4H); 1.12-1.28 (m, 4H); 1.51-1.69 (m, 8H); 1.72-1.82 (m, 2H); 1.90-2.02 (m, 2H); 2.13-2.23 (m, 2H); 2.42 (dd, 1H, J=4.88, 1.71 Hz); 2.46 (dd, 1H, J=4.88, 1.95 Hz); 9.73 (dd, 2H, J=2.81, 2.08 Hz).
$^{13}$C NMR (101 MHz, CHLOROFORM-d) ppm: 16.74 (q, 1C); 17.03 (q, 1C); 19.56 (q, 1C); 19.58 (q, 1C); 19.79 (q, 1C); 19.81 (q, 1C); 26.37 (t, 1C); 26.45 (t, 1C); 28.84 (d, 1C); 29.46 (t, 1C); 29.51 (t, 1C); 29.96 (t, 1C); 32.64 (t, 1C); 33.01 (d, 1C); 33.02 (d, 1C); 33.16 (d, 2C); 33.66 (t, 1C); 42.73 (d, 1C); 42.83 (d, 1C); 44.01 (d, 1C); 44.10 (d, 1C); 48.39 (t, 1C); 48.64 (t, 1C); 203.36 (d, 1C); 203.40 (d, 1C).
MS: m/z (relative intensity) (no M+), 178 (2), 163 (2), 152 (49), 135 (24), 125 (9), 123 (13), 109 (74), 95 (13), 93 (12), 82 (100), 69 (77), 67 (41), 55 (39), 41 (49).

EXAMPLE 5

Preparation of 3-(3-isopropylcyclohexyl)-2-methylbutanal i) 3-(3-isopropylcyclohexyl)-2-methylenebutanal

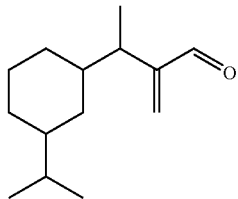

A solution of 3-(3-isopropylcyclohexyl)butanal (6 g, 30.5 mmol) in isopropanol (3.5 mL) followed by formaldehyde (37% wt in water, 30.5 mmol, 1 eq) was charged into a 50 mL three-necked round-bottom flask equipped with a reflux condenser and a mechanical stirrer. Propionic acid (228 L, 3.0 mmol, 0.1 eq) and pyrrolidine (255 L, 3.0 mmol, 0.1 eq) were added at ambient temperature. The reaction mixture was then stirred at 45° C. for 3 h. The crude mixture was cooled to ambient temperature dissolved in MTBE (100 mL) and washed with saturated aqueous NaHCO₃ (100 mL), brine (100 mL), dried over magnesium sulphate and concentrated. The crude product was chromatographed on a silica gel column with 3% EtOAc in hexane as elution agent giving 3-(3-isopropylcyclohexyl)-2-methylenebutanal (5 g, gc purity>99%; yield 78%).

Odour: woody, fruity, green, aldehydic.

Analytical Data (2 Isomers):
$^1$H NMR (400 MHz, CHLOROFORM-d) ppm: 0.48-1.82 (m, 40H), 2.50-2.63 (m, 2H), 5.98-6.03 (m, 2H), 6.17-6.22 (m, 2H), 9.48-9.53 (m, 2H).
$^{13}$C NMR (101 MHz, CHLOROFORM-d) ppm: 15.87 (q, 1C), 16.08 (q, 1C), 19.49 (q, 2C), 19.85 (q, 2C), 26.32 (t, 1C), 26.40 (t, 1C), 29.10 (t, 1C), 29.27 (t, 1C), 29.29 (t, 1C), 31.28 (t, 1C), 32.77 (t, 1C), 32.99 (d, 1C), 33.07 (d, 1C), 34.82 (t, 1C), 36.72 (d, 1C), 36.75 (d, 1C), 41.40 (d, 1C), 41.62 (d, 1C), 43.88 (d, 1C), 44.00 (d, 1C), 133.97 (t, 2C), 154.69 (s, 1C), 154.73 (s, 1C), 194.78 (d, 1C), 194.80 (d, 1C).
MS: Minor isomer: m/z (relative intensity) 208 (M+, 1), 193 (1), 165 (3), 147 (7), 125 (62), 109 (5), 105 (4), 95 (5), 91 (6), 83 (47), 69 (100), 55 (35), 41 (33).
Minor intensity m/z (relative intensity): 208 (M+, 1), 193 (1), 165 (2), 147 (5), 125 (63), 109 (4), 105 (4), 95 (4), 91 (5), 83 (47), 69 (100), 55 (33), 41 (31).

ii) 3-(3-isopropylcyclohexyl)-2-methylbutanal

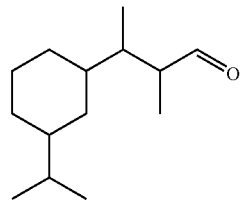

5% Pd/C (250 mg, 5% w/w) was charged into a 25 mL autoclave vessel with 3-(3-isopropylcyclohexyl)-2-methylenebutanal (4.5 g, 21.6 mmol) in methanol (5 mL). The mixture was vigorously stirred under an hydrogen atmosphere (10 Bar) at 40-45° C. for 40 minutes. The catalyst was filtered over celite and the solution was concentrated. The resulting crude product was distilled with a bulb-to-bulb distillation (2.5 mBar, 117° C.) to give 3-(3-isopropylcyclohexyl)-2-methylbutanal (3 g, gc purity>90%; yield=67%).

Odour: green, violet, apple, cucumber.

Analytical Data (2 Isomers):
$^1$H NMR (400 MHz, CHLOROFORM-d) ppm: 0.57-0.79 (m, 2H), 0.79-0.93 (m, 18H), 0.95 (dd, 2H, J=6.96, 2.81 Hz), 1.01-1.05 (m, 6H), 1.06-1.31 (m, 4H), 1.31-1.46 (m, 5H), 1.46-1.70 (m, 8H), 1.70-1.86 (m, 3H), 2.27-2.56 (m, 2H), 9.60-9.64 (m, 2H).
$^{13}$C NMR (101 MHz, CHLOROFORM-d) ppm: 11.67 (q, 1C), 11.70 (q, 1C), 13.95 (q, 1C), 14.05 (q, 1C), 19.51 (q, 1C), 19.62 (q, 1C), 19.80 (q, 1C), 19.83 (q, 1C), 26.39 (t, 1C), 26.58 (t, 1C), 28.03 (t, 1C), 29.37 (t, 1C), 29.52 (t, 1C), 31.73 (t, 1C), 31.80 (t, 1C), 33.00 (d, 1C), 33.03 (d, 1C), 35.30 (t, 1C), 39.26 (d, 1C), 39.42 (d, 1C), 39.76 (d, 1C), 39.77 (d, 1C), 44.01 (d, 1C), 44.30 (d, 1C), 49.69 (d, 1C), 49.82 (d, 1C), 206.04 (d, 1C), 206.09 (d, 1C).
MS: Major isomer: m/z (relative intensity) 210 (M+, <1), 192 (1), 177 (2), 152 (48), 149 (14), 123 (12), 109 (66), 97 (14), 95 (15), 82 (100), 69 (82), 55 (47), 41 (49).

EXAMPLE 6

Preparation of 3-(3-tert-butylcyclohexyl)butanal i) 3-(3-tert-butylphenyl)butanal

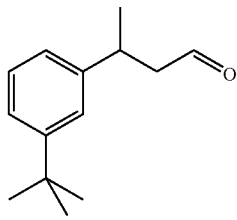

In a 1 L three-necked round-bottom flask equipped with a mechanical stirrer and a reflux condenser were introduced DMF (200 mL), 1-bromo-3-tert-butylbenzene (54.3 g, 0.25 mol), crotyl alcohol (65 mL, 0.76 mol, 3 eq), sodium carbonate (66.2 g, 0.62 mol, 2.5 eq), tetrabutyl ammonium bromide (69.5 g, 0.25 mol, 1 eq), palladium acetate (5.05 g, 7.5 mmol, 3 mol %) and tri-o-tolyl phosphine (7.6 g, 25 mmol, 0.1 eq). After stirring for 1 h at 90-100° C., the reaction mixture was cooled to ambient temperature. The reaction mixture was filtered over celite. The organic phase thus obtained was diluted with MTBE (500 mL) and washed three times with water (500 mL portions), dried over magnesium sulphate and concentrated. The resulting crude product was distilled with a bulb-to-bulb distillation (3 mBar, 121° C.) to give a colourless oil (34.7 g, gc purity 73%). The crude product was chromatographed on a silica gel column with 5% EtOAc in hexane as elution agent giving 3-(3-tert-butylphenyl)butanal (12.3 g, gc purity 99%; yield 39%).

Odour: floral, aldehydic, muguet, marine.

Analytical Data:

$^1$H NMR (400 MHz, CHLOROFORM-d) ppm: 1.33 (d, 3H, J=5.86 Hz); 1.32 (s, 9H); 2.61-2.80 (m, 2H); 3.36 (qt, 1H, J=7.16, 6.96 Hz); 7.01-7.07 (m, 1H); 7.23-7.27 (m, 3H); 9.72 (t, 1H, J=2.08 Hz).

$^{13}$C NMR (101 MHz, CHLOROFORM-d) ppm: 22.15 (q, 1C); 31.35 (q, 3C); 34.53 (d, 1C); 34.66 (s, 1C); 51.83 (t, 1C); 123.49 (d, 1C); 123.55 (d, 1C); 123.91 (d, 1C); 128.30 (d, 1C); 145.06 (s, 1C); 151.48 (s, 1C); 202.04 (d, 1C).

MS: m/z (relative intensity) 204 (M$^+$, 12), 189 (31), 171 (4), 161 (30), 147 (100), 145 (81), 130 (17), 119 (24), 117 (23), 115 (21), 105 (25), 91 (36), 77 (14), 65 (8), 57 (52), 41 (31).

ii) 3-(3-text-butylcyclohexyl)butan-1-ol

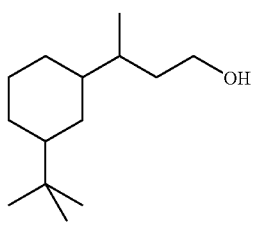

5% Ru/Al$_2$O$_3$ (75 mg, 5% w/w) was charged into a 25 mL autoclave vessel with 3-(3-tert-butylphenyl)butanal (1.5 g, 52 mmol). The mixture was vigorously stirred under an hydrogen atmosphere (60-65 Bar) at 130° C. for 10 h. The reaction mixture was filtered, rinsed with cyclohexane and concentrated. The resulting crude product was distilled with a bulb-to-bulb distillation (0.5 mBar, 125-135° C.) to give 3-(3-tert-butylcyclohexyl)butan-1-ol (1 g, gc purity>99%; yield 62%).

Odour: odourless.

Analytical Data (2 Isomers):

$^1$H NMR (400 MHz, CHLOROFORM-d) ppm: 0.63-0.80 (m, 2H); 0.81-0.87 (m, 6H); 0.83 (s, 18H); 0.87-1.88 (m, 26H); 3.54-3.80 (m, 4H).

$^{13}$C NMR (101 MHz, CHLOROFORM-d) ppm: 15.91 (q, 1C); 16.35 (q, 1C); 26.84 (t, 1C); 26.93 (t, 1C); 27.50 (t, 1C); 27.51 (t, 1C); 27.57 (q, 3C); 27.58 (q, 3C); 28.08 (t, 1C); 29.72 (t, 1C); 29.93 (t, 1C); 31.57 (t, 1C); 32.54 (s, 1C); 32.57 (s, 1C); 34.70 (d, 1C); 34.71 (d, 1C); 36.85 (t, 1C); 37.40 (t, 1C); 43.08 (d, 1C); 43.31 (d, 1C); 48.27 (d, 1C); 48.35 (d, 1C); 61.65 (t, 1C); 61.73 (t, 1C).

MS: Minor isomer: m/z (relative intensity) (no M$^+$), 197 (1), 194 (2), 179 (1), 166 (23), 155 (30), 137 (30), 123 (11), 110 (43), 109 (41), 95 (62), 83 (35), 81 (94), 69 (44), 67 (48), 57 (100), 41 (56).

Major isomer: m/z (relative intensity) (no M$^+$), 197 (1), 194 (2), 179 (1), 166 (26), 155 (35), 137 (34), 123 (13), 110 (46), 109 (44), 95 (64), 83 (36), 81 (97), 69 (45), 67 (49), 57 (100), 41 (56).

iii) 3-(3-tert-butylcyclohexyl)butanal

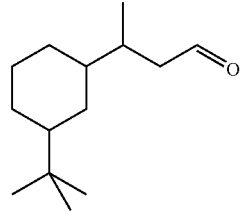

A solution of Dess Martin periodinane (1.8 g, 4.2 mmol, 1.1 eq) in dichloromethane (30 mL) was charged into a 250 mL three-necked round-bottom flask, equipped with a mechanical stirrer and a reflux condenser. 3-(3-tert-butylcyclohexyl)butan-1-ol (805 mg, 3.79 mmol) was added dropwise, followed by a mixture of water (75 L) in dichloromethane (75 mL) at ambient temperature, over 1.5 h. After stirring for 2 h at ambient temperature, the mixture was diluted with diethyl ether (100 mL) and washed with a 1:1 mixture of saturated aqueous NaHCO$_3$ and 10% aqueous Na$_2$S$_2$O$_3$ (50 mL) and brine (50 mL). The organic phase was dried over magnesium sulphate and concentrated. The crude product was chromatographed on a silica gel column with 5% EtOAc in hexane as elution agent giving 3-(3-text-butylcyclohexyl)butanal (100 mg, gc purity>93%; yield 13%).

Odour: aldehydic, floral, herbal, watery.

Analytical Data (2 Isomers):

$^1$H NMR (400 MHz, CHLOROFORM-d) ppm: 0.60-1.95 (m, 20H); 0.82 (s, 18H); 0.89-0.92 (t, 6H); 1.93 (m, 2H); 2.15-2.47 (m, 4H); 9.74 (m, 2H).

$^{13}$C NMR (101 MHz, CHLOROFORM-d) ppm: 16.67 (q, 1C); 17.19 (q, 1C); 26.63 (t, 1C); 26.71 (t, 1C); 27.34 (t, 2C); 27.54 (q, 6C); 28.61 (t, 1C); 29.75 (t, 1C); 30.34 (t, 1C); 31.33 (t, 1C); 32.54 (s, 1C); 32.55 (s, 1C); 33.28 (d, 1C); 33.31 (d, 1C); 43.01 (d, 1C); 43.16 (d, 1C); 48.11 (d, 1C); 48.18 (d, 1C); 48.33 (t, 1C); 48.78 (t, 1C); 203.44 (s, 1C); 203.50 (s, 1C).

MS: Minor isomer: m/z (relative intensity): (no M+), 177 (4), 166 (19), 135 (26), 121 (8), 109 (54), 95 (23), 93 (15), 81 (37), 79 (22), 67 (42), 57 (76), 55 (38), 41 (100), 39 (49).

Major isomer: m/z (relative intensity): (no M+), 177 (4), 166 (19), 135 (26), 121 (8), 109 (46), 95 (22), 93 (14), 81 (33), 79 (19), 67 (40), 57 (68), 55 (31), 41 (100), 39 (45).

EXAMPLE 7

Preparation of 2-methyl-3-(3-methylcyclohexyl)propanal i) (2E)-2-methyl-3-(3-methylphenyl)acrylaldehyde

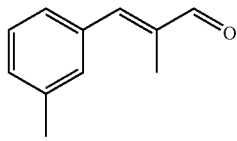

A solution of potassium hydroxide (24 g, 0.36 mol, 0.6 eq, with a purity of 85%) in ethylene glycol (120 g) and water (12 g) was charged into a 500 mL three-necked round-bottom flask equipped with a reflux condenser and a mechanical stirrer. 3-methyl benzaldehyde (70 g, 0.59 mol) was added dropwise. The stirred reaction mixture was heated at 38-42° C. and propionaldehyde (41 g, 0.71 mol, 1.2 eq) was dosed in over 3.25 h. After a further hour at 40° C., the reaction mixture was cooled to ambient temperature and the two layers separated. The organic layer thus obtained was washed with water (2×100 mL), dried over magnesium sulphate and concentrated. The resulting crude product was distilled via a Vigreux column (1.0 mBar, 87-92° C.), to give (2E)-2-methyl-3-(3-methylphenyl)acrylaldehyde (65.9 g, gc purity>95%; yield 70%).

Odour: spicy, cinnamon.

Analytical Data:

$^1$H NMR (400 MHz, CHLOROFORM-d) ppm: 2.09 (d, 3H); 2.42 (s, 3H); 7.20-7.38 (m, 5H); 9.59 (s, 1H).

$^{13}$C NMR (101 MHz, CHLOROFORM-d) ppm: 10.92 (q, 1C); 21.37 (q, 1C); 127.08 (d, 1C); 128.54 (d, 1C); 130.33 (d, 1C); 130.70 (d, 1C); 135.05 (s, 1C); 138.13 (s, 1C); 138.31 (s, 1C); 150.03 (d, 1C); 195.55 (d, 1C).

MS: m/z (relative intensity): 160 (M+, 25), 159 (22), 145 (100), 131 (12), 128 (14), 117 (60), 115 (60), 105 (5), 91 (42), 77 (13), 65 (13), 63 (14), 51 (14), 39 (25).

ii) 2-methyl-3-(3-methylcyclohexyl)propan-1-ol

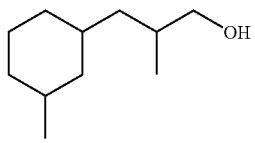

5% Ru/Al$_2$O$_3$ (630 mg, 2.7% w/w) was charged into a 50 mL autoclave vessel with (2E)-2-methyl-3-(3-methylphenyl)acrylaldehyde (23.5 g, 0.15 mol). The mixture was vigorously stirred under an hydrogen atmosphere (45-50 Bar) at 160° C. for 7 h. The catalyst was filtered and the solution was rinsed with cyclohexane and concentrated. The resulting crude product was distilled via a Vigreux column (5 mBar, 102-104° C.) to give 2-methyl-3-(3-methylcyclohexyl)propan-1-ol (13.7 g, gc purity>81%; yield 60%).

Odour: floral, muguet, citrus.

Analytical Data (2 Isomers):

$^1$H NMR (400 MHz, CHLOROFORM-d) ppm: 0.4-1.8 (m, 28H); 0.83-0.90 (m, 12H); 3.32-3.35 (m, 4H).

$^{13}$C NMR (101 MHz, CHLOROFORM-d) ppm: 16.84 (q, 1C); 16.845 (q, 1C); 22.92 (q, 1C); 22.94 (q, 1C); 26.26 (t, 1C); 26.34 (t, 1C); 32.58 (d, 1C); 32.60 (d, 1C); 32.62 (d, 1C); 32.72 (d, 1C); 33.84 (t, 2C); 34.79 (d, 1C); 34.81 (d, 1C); 35.32 (t, 2C); 41.19 (t, 1C); 41.21 (t, 1C); 41.96 (t, 1C); 43.16 (t, 1C); 68.73 (t, 1C); 68.74 (t, 1C).

MS: Major isomer: m/z (relative intensity) (no M+), 152 (7), 137 (7), 123 (5), 110 (41), 97 (46), 95 (100), 82 (44), 81 (52), 69 (32), 67 (24), 55 (97), 41 (34).

Minor isomer: m/z (relative intensity) (no M+), 152 (5), 137 (6), 123 (5), 110 (39), 97 (35), 95 (100), 82 (43), 81 (53), 69 (29), 67 (24), 55 (89), 41 (34).

iii) 2-methyl-3-(3-methylcyclohexyl)propanal

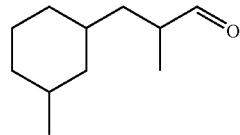

A solution of Dess Martin periodinane (4.1 g, 9.7 mmol, 1.1 eq) in dichloromethane (43 mL) was charged into a 250 mL three-necked round-bottom flask, equipped with a mechanical stirrer and a reflux condenser. 2-methyl-3-(3-methylcyclohexyl)propan-1-ol (1.5 g, 8.8 mmol) was added dropwise, followed by a mixture of water (127 L) in dichloromethane (127 mL) at ambient temperature, over 1 h. After stirring for 1 h at ambient temperature, the mixture was diluted with diethyl ether (100 mL) and washed with a 1:1 mixture of saturated aqueous NaHCO$_3$ and 10% aqueous Na$_2$S$_2$O$_3$ (50 mL) and brine (50 mL), dried over magnesium sulphate and concentrated. The crude product was chromatographed on a silica gel column with 5% EtOAc in hexane as elution agent giving 2-methyl-3-(3-methylcyclohexyl)propanal (800 mg, gc purity>90%; yield 54%).

Odour: floral, citrus, cuminic, nitrile.

Analytical Data (2 Isomers):

$^1$H NMR (400 MHz, CHLOROFORM-d) ppm: 0.4-1.8 (m, 24H); 0.84 (d, 6H); 1.04 (d, 6H); 2.30-2.60 (m, 2H); 9.56 (d, 2H).

$^{13}$C NMR (101 MHz, CHLOROFORM-d) ppm: 13.74 (q, 1C); 13.76 (q, 1C); 22.81 (q, 1C); 22.83 (q, 1C); 26.08 (t, 1C); 26.13 (q, 1C); 32.52 (d, 2C); 32.57 (t, 1C); 33.22 (t, 1C); 34.99 (d, 1C); 35.02 (d, 1C); 35.12 (t, 1C); 35.17 (t, 1C); 38.31 (t, 1C); 38.35 (t, 1C); 41.85 (t, 1C); 42.49 (t, 1C); 43.72 (d, 1C); 43.74 (d, 1C); 205.58 (s, 2C).

MS: Major isomer: m/z (relative intensity) 168 (M+, 1), 150 (5), 135 (10), 125 (6), 111 (68), 110 (58), 97 (26), 95 (63), 83 (17), 82 (22), 81 (27), 69 (59), 67 (22), 58 (36), 55 (100), 41 (41).

Minor isomer: m/z (relative intensity) 168 (M+, <1), 150 (3), 135 (12), 125 (5), 110 (60), 97 (22), 95 (75), 83 (15), 82 (26), 81 (32), 69 (63), 67 (26), 58 (40), 55 (100), 41 (45).

EXAMPLE 8

Preparation of 2,2-dimethyl-3-(3-methylcyclohexyl)propanal i) 2,2-dimethyl-3-(3-methylcyclohexyl)propan-1-ol

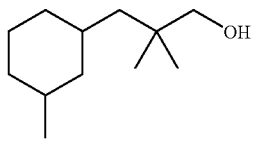

5% Rh/C (450 mg, 15% w/w) was charged into a 50 mL autoclave vessel containing a mixture of 2,2-dimethyl-3-(3-methylphenyl)propan-1-ol (6 g, 34 mmol) in water (17 mL). The mixture was vigorously stirred under an hydrogen atmosphere (10 Bar) at 60° C. for 6 h. The reaction mixture was filtered and the filtrate was extracted with MTBE (25 mL), dried over magnesium sulphate and concentrated. The resulting crude product was distilled with a bulb-to-bulb distillation (2.5 mBar, 90° C.) to give 2,2-dimethyl-3-(3-methylcyclohexyl)propan-1-ol (5.1 g, gc purity>99%; yield 82%).

Odour: aldehydic, fatty/greasy, floral.

Analytical Data:

$^1$H NMR (400 MHz, CHLOROFORM-d) ppm: 0.51-0.88 (m, 2H), 0.79-0.87 (m, 9H), 0.95-1.76 (m, 10H), 1.87 (br. s., 1H), 3.25 (s, 2H).

$^{13}$C NMR (101 MHz, CHLOROFORM-d) ppm: 22.90 (q, 1C), 24.30 (q, 1C), 24.31 (t, 1C), 26.53 (d, 1C), 32.90 (d, 1C), 33.58 (t, 1C), 34.83 (t, 1C), 35.48 (t, 1C), 35.68 (s, 1C), 44.95 (t, 1C), 46.26 (t, 1C), 72.32 (t, 1C).

MS: Major isomer: m/z (relative intensity) (no M$^+$), 153 (34), 137 (3), 111 (11), 97 (100), 83 (29), 69 (20), 55 (74), 41 (23).

Minor isomer m/z (relative intensity): (no M$^+$), 153 (33), 137 (6), 111 (11), 97 (100), 83 (30), 69 (23), 55 (79), 41 (25).

ii) 2,2-dimethyl-3-(3-methylcyclohexyl)propanal

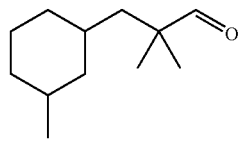

A solution of Dess Martin periodinane (9.0 g, 21.1 mmol, 1.3 eq) in dichloromethane (165 mL) was charged into a 250 mL three-necked round-bottom flask, equipped with a mechanical stirrer and a reflux condenser. The solution was cooled to 0° C. by the mean of an ice/salt bath. 2,2-dimethyl-3-(3-methylcyclohexyl)propan-1-ol (3.0 g, 16.3 mmol) was added dropwise. After stirring for 2 h at ambient temperature, the mixture was cooled down to −15° C. and the solid was filtered off. The organic solution was then concentrated. The resultant crude product was chromatographed on a silica gel column with 2% EtOAc in hexane as elution agent giving 2,2-dimethyl-3-(3-methylcyclohexyl)propanal (1.0 g, gc purity>85%; yield 33%).

Odour: marine, watery.

Analytical Data:

$^1$H NMR (400 MHz, CHLOROFORM-d) ppm: 0.45-0.79 (m, 2H), 0.81 (d, 3H, J=6.59 Hz), 1.02 (s, 6H), 1.10-1.79 (m, 10H), 9.45 (t, 1H).

$^{13}$C NMR (101 MHz, CHLOROFORM-d) ppm: 21.98 (q, 1C), 22.09 (q, 1C), 22.81 (q, 1C), 26.22 (t, 1C), 32.66 (d, 1C), 34.13 (t, 1C), 34.20 (d, 1C), 34.77 (t, 1C), 43.47 (t, 1C), 45.78 (t, 1C), 45.94 (s, 1C), 206.80 (d, 1C).

MS: Major isomer: m/z (relative intensity) 182 (M$^+$, <1), 164 (2), 153 (15), 135 (2), 125 (4), 111 (21), 97 (100), 83 (28), 72 (94), 69 (30), 55 (89), 41 (32).

EXAMPLE 9

Odour Intensity 3-(3-tert-butylcyclohexyl)propanal, hereafter referred to as Compound 1, was diluted in DPG to a level of 10 wt %. For comparison a 10 wt % solution in DPG of Florhydral™, and a neat Lily Aldehyde™ composition were prepared.

The three compositions were added to a smelling strip and the odour intensity was assessed by a number of professional perfumers. All the perfumers indicated that the Compound 1 had a more intense odour than the Lily Aldehyde™ and Florhydral™.

EXAMPLE 10

Performance on Hair

Pantene™ shampoo was dosed at 0.2%-80 mg of ingredient was added to 40 g of Pantene™ shampoo base. Pantene™ shampoo dosed with 0.2% Lily Aldehyde™ was used as the standard (scale 0 to 10; Lily Aldehyde™=5). Unperfumed Pantene™ was used for the control.

"Caucasian European" origin switches were used. Switches were wetted and 10% by weight of the dry hair switch was added in product. The shampoo was massaged in to the hair switch for 30 s. The muguet odour intensity (foaming intensity) was then assessed. The switches were rinsed under hand hot warm water and towel dried. The muguet odour intensity (damp intensity) was then assessed. The hair switches were line dried for 3 hours in an odour free room. The muguet odour intensity (dry intensity) was then assessed.

| INGREDIENT | DRY INTENSITY | | DAMP INTENSITY | | FOAMING INTENSITY | |
|---|---|---|---|---|---|---|
| | MEAN | RANGE | MEAN | RANGE | MEAN | RANGE |
| LILY ALDEHYDE | 5 | — | 5 | — | 5 | — |
| Compound 1 10% DPG | 8 | 7-10 | 8 | 7-10 | 9 | 7-10 |
| FLORHYDRAL 10% DPG | 4 | 2-7 | 6 | 4-8 | 5 | 4-6 |

Compound 1 outperformed Florhydral™ in Pantene™ shampoo. It showed very linear performance on foaming, damp and dry hair and proved much more substantive on dry hair than any of the benchmarks.

EXAMPLE 11

Performance in Ariel™ High Suds (Handwash Powder)

Ariel™ high suds were dosed at 0.1%-20 mg of ingredient were added to 20 g of powder; Ariel™ high suds dosed with 0.1% Lily Aldehyde™ was used as the standard. Unperfumed Ariel™ high suds was used for the control.

The bloom from bowl was assessed by dissolving 4.5 g of Ariel™ high suds in 2 liters of tepid water, in a plastic bowl. Two terry toweling cloths were stirred in the solution for 5 minutes. The wash solution was assessed (scale 0 to 10; Lily Aldehyde™=5), giving the intensity from bowls figure. One cloth was rinsed in tepid water, hand wringed and odour assessed for rinsed cloth intensity (scale as above).

| INGREDIENT | INTENSITY FROM BOWLS MEAN | RANGE | INTENSITY RINSED CLOTH MEAN | RANGE |
|---|---|---|---|---|
| LILY ALDEHYDE | 5 | — | 5 | — |
| Compound 1 10% DPG | 5 | 3-7 | 8 | 7-8 |
| FLORHYDRAL 10% DPG | 3 | 2-4 | 4 | 2-6 |

Ariel™ high suds containing Compound 1 showed greater intensity than Florhydral™. Rinsed cloth with Ariel™ high suds containing Compound 1 outperformed the benchmarks, indicating good substantivity on cloth.

EXAMPLE 12

Performance in Candle Wax

Candle wax house base (IGI hard paraffin wax mix) was dosed at 1.0%—candles were left to mature at room temperature for 24 hours before assessment. All ingredients were used as 10% dilutions in benzyl benzoate. Intensity was assessed, by a panel of perfumers, from candle placed in fragrance booths for one hour. All candles were first evaluated in the cold wax before burning. Candles were then burned for one hour, in the fragrance booth, and odour assessed again for the burn mode intensity.

Compound 1 was much stronger than all of the benchmarks, both in cold wax and in burn mode.

EXAMPLE 13

Insect Repellency

Results

Compound 1 was tested for insect repellency against mosquitoes and ants. In all cases, repellency is calculated with reference to an untreated surface having 0% repellency.

Tests results showed an excellent repellency against mosquitoes (100% repellency after 10 minutes, wrt untreated surface).

Compound 1 showed very good activity against ants (72% repellency over first hour, wrt untreated surface).

Protocols:

Ant test is completed with a simplified general purpose cleaner formulation:

| | |
|---|---|
| Synperonic 91-6 | 5.0% |
| Perfume.ingredient | 1.0% |
| Water | 94.0% |

This product is applied to the floor tiles (vinyl) at the rate of 20 g·m$^{-2}$.

Ant (*Lasius niger*)

300 mm square vinyl tiles half treated with 0.9 ml test material and left for 2 hours.

Glass arena 250 mm square, 75 mm high and fluon coated, open to air.

Arena illuminated from 1.0 m above by four 18 W fluorescent lamps.

50 black ants per arena counted every 5 minutes.

Arena turned 180 degrees every 10 minutes.

Any ants injured or escaping replaced.

Mosquito (*Aedes aegyptii*)

A perspex box approx 18 inch cube, with sleeved circular entry was used as the test cage.

The box contained 5 day old, mated honey fed females.

The area of arm to be tested was measured.

The test material was applied from ethanol solution at a rate of 0.2 mg test material per square centimeter.

A similar area of the other arm was used for the control.

A pair of disposable gloves was worn on the hands throughout the test.

In turn each arm was inserted into the cage for 30 seconds. This was repeated 3 times.

The number of mosquitoes landing on the arm was recorded every five seconds.

As penetration of the skin occurs within 5 seconds the arm was flicked at this frequency to dislodge the flies.

| INGREDIENT | COLD WAX MODE | BURN MODE |
|---|---|---|
| LILY ALDEHYDE 10% BENZYL BENZOATE | Faint odour character, no comparison to Compound 1. | Not strong. Does not compare to the strength of Compound 1. |
| COMPOUND 1 10% BENZYL BENZOATE | Very strong in cold wax, excellent strength. | VERY strong, excellent performer for strength in burn mode. |
| FLORHYDRAL 10% BENZYL BENZOATE | Not as strong as Compound 1. Still a nice watery floral note in cold wax. | Not as strong as Compound 1. |
| LYRAL 10% BENZYL BENZOATE | Faint odour character in cold mode. | Very weak in burn. |

EXAMPLE 14

Antimicrobial

Minimum Inhibitory Concentration (MIC)

One property that characterises the effectiveness of a compound or composition to inhibit the growth of bacteria, is the minimum inhibitory concentration, or MIC, of the compound or composition. The MIC is defined as the minimum amount of a compound or composition (e.g. in ppm) at which little or no bacterial growth is observed. Generally, the lower the MIC of a compound or composition for a bacterium, the more effective the compound will be at inhibiting bacterial growth.

The minimum inhibitory concentration of a compound was determined by the following method.

A culture of the test strains of bacteria *Staphylococcus aureus* ATCC 6538 (American Type Culture Collection, P.O. Box 1549, Manassas, Va. 20108, USA) was incubated for 16-24 hours, in a shaken flask at 37° C. The cultures was then diluted in sterile 0.1% TSB (Oxoid, Basingstoke, UK) to give a concentration of bacteria of approximately $10^6$ colony forming units (cfu) per ml.

Fragrance compounds were prepared in sterile TSB to give stock solutions with final concentrations of 40,000 ppm. The absorbance at 540 nm (hereinafter referred to for brevity and simplicity as "$A_{540}$") was used as a measure of turbidity resulting from bacterial growth. The MIC was taken as the concentration of ingredient required to inhibit growth so that the average change in absorbance during the incubation period was <0.2 $A_{540}$.

The results are shown below.

| Material | Known as | MIC (ppm) |
| --- | --- | --- |
| 3-(3-tert-butylcyclolaexyl)propanal | Compound 1 | 312 (156) |
| 3-(3-isopropylcyclohexyl)butanal | Compound 2 | 312 (156) |
| 2-methyl-3-(3-methylcyclohexyl)propanal | Compound 3 | 5000 |
| 3-(3-methylcyclohexyl)propanal | Compound 4 | >5000 |

EXAMPLE 15

Malodour Counteracting

Fragrance materials were tested using small-scale tabletop method (3 mL malodour in 15 mL jar+1 mL material oil in 15 mL jar both placed in 500 mL jar (where either fragrance or malodour is tested alone DEP should be placed in the other 15 mL jar). Bathroom malodour is used at 0.5%.

The perceived intensity of malodour and fragrance in each jar is assessed by a trained sensory panel using a line scale anchored at the extremes (0-100). The malodour control is used as a standard (perceived intensity 75) against which all other perceived intensities are scaled.

A further jar was prepared as "hidden controls", also containing malodour only, but the panellists are unaware that it does not contain a fragranced, or active, product.

Compounds 3 and 4 were tested for malodour counteracting performance when at 1% w/w in DPG. They significantly reduced the perceived intensity of malodour and have similar performance as Cyprisate™ and Camonal™, which are well-known malodour counteractants.

EXAMPLE 16

Perfumed Products

A perfuming composition for a water based gel air freshener was prepared by admixing the following ingredients:

| INGREDIENT | % |
| --- | --- |
| ADOXAL | 0.2 |
| AMYL SALICYLATE | 3 |
| ANISIC ALDEHYDE | 0.5 |
| ANTHER[1] | 2 |
| BENZYL ACETATE | 10 |
| BENZYL SALICYLATE | 4 |
| CYCLAMEN ALDEHYDE | 4 |
| DIHYDRO MYRCENOL | 13.2 |
| EFETAAL[2] | 2 |
| ELINTAAL[3] | 2 |
| FLOROCYCLENE[4] | 5 |
| FLOROSA[5] | 5 |
| HERBANATE[6] | 1 |
| HEXYL SALICYLATE | 4 |
| INDOLE | 0.1 |
| JASMACYCLENE[7] | 5 |
| JASMATONE[8] | 5 |
| LAVANDIN | 5 |
| LIGUSTRAL[9] | 1 |
| LITSEA CUBEBA | 1 |
| METHYL DIHYDRO JASMONATE[10] | 2 |
| ORTHOLATE[11] | 5 |
| PELARGENE[12] | 0.5 |
| PHENYL ACETALDEHYDE DIMETHYL ACETAL | 3 |
| PHENYL ACETIC ALDEHYDE 50% PEA | 0.5 |
| PHENYL ETHYL ACETATE | 3.5 |
| PHENYL ETHYL ALCOHOL | 5 |
| SAGE DALMATIAN | 0.5 |
| SILVANONE[13] | 1 |
| TERPINEOL | 5 |
| TOP ROSE AB[14] | 1 |
| TOTAL QUANTITY | 100 |

[1]1-(2-((3-methylbutyl)oxy)ethyl)benzene; origin: Quest International, UK.
[2]1-(2-((1-(ethyloxy)ethyl)oxy)ethyl)benzene; origin: Quest International, UK.
[3]3-((1-ethyloxy)ethyl)oxy)-3,7-dimethyl-1,6-octadiene; origin: Quest International, UK.
[4]3a,4,5,6,7,7a-hexahydro-4,7-methano-1H-inden-6-yl propanoate; origin: Quest International, UK.
[5]4-methyl-2-(2-methylpropyl)tetrahydro-2H-4-pyranol: Quest International, UK.
[6]ethyl 3-isopropylbicyclo[2.2.1]hept-5-ene-2-carboxylate; origin: Quest International, UK.
[7]tricyclo[5.2.1.0 2,6]dec-4-en-8-yl ethanoate; origin: Quest International, UK.
[8]2-hexylcyclopentan-1-one; origin: Quest International, UK.
[9]cis and trans 2,4-dimethyl-3-cyclohexene-1-carbaldehyde; origin: Quest International, UK.
[10]methyl 2-(3-oxo-2-pentylcyclopentyl)ethanoate; origin: Quest International, UK.
[11]2-(1,1-dimethylethyl)cyclohexyl ethanoate; origin: Quest International, UK.
[12]3,6-dihydro-4,6-dimethyl-2-phenyl-2H-pyran; origin: Quest International, UK.
[13]mixture of oxacycloheptadecan-2-one and cyclopentadecanone; origin: Quest International, UK.
[14]compounded perfumery base; origin: Quest International, UK.

The addition of 0.25% of Compound 1 to the above-described perfuming composition, instead of an equivalent amount of Dihydro Myrcenol, enhanced the perceived odour intensity of the fragrance and imparted freshness, white/floralcy to the composition.

A perfuming composition for a general purpose cleaner was prepared by admixing the following ingredients:

| INGREDIENT | % |
| --- | --- |
| 10%* ALLYL AMYL GLYCOLATE | 0.2 |
| BENZYL ACETATE | 1 |
| CIS 3 HEXENOL | 1 |
| CIS 3 HEXENYL ACETATE | 1 |
| CYCLAMEN ALDEHYDE | 2 |
| DIHYDRO MYRCENOL | 5 |
| DUPICAL[1] | 0.3 |
| EFETAAL[2] | 2 |
| ELINTAAL[3] | 3 |
| FLOROSA[4] | 10 |
| GERANYL ACETATE | 5 |
| INDOLE | 0.2 |
| JASMATONE[5] | 3 |
| LINALOL | 26.3 |

-continued

| INGREDIENT | % |
|---|---|
| MEFROSOL[6] | 20 |
| METHYL DIHYDRO JASMONATE[7] | 2 |
| PHENYL ETHYL ALCOHOL | 10 |
| PHENYL PROPYL ALCOHOL | 3 |
| TETRAHYDRO GERANIOL | 5 |
| TOTAL QUANTITY | 100 |

*in dipropyleneglycol
[1]4-tricyclo(5.2.1.0 2,6)dec-8-ylidenbutanal; origin: Quest International, UK.
[2]1-(2-((1-(ethyloxy)ethyl)oxy)ethyl)benzene; origin: Quest International, UK.
[3]3-((1-ethyloxy)ethyl)oxy)-3,7-dimethyl-1,6-octadiene; origin: Quest International, UK.
[4]4-methyl-2-(2-methylpropyl)tetrahydro-2H-4-pyranol: Quest International, UK.
[5]2-hexylcyclopentan-1-one; origin: Quest International, UK.
[6]3-methyl-5-phenylpentanol; origin: Quest International, UK.
[7]methyl 2-(3-oxo-2-pentylcyclopentyl)ethanoate; origin: Quest International, UK.

The addition of 0.50% of Compound 1 to the above-described perfuming composition, instead of an equivalent amount of Linalol, enhanced the perceived odour intensity of the fragrance and imparted freshness, white/floralcy to the composition.

The invention claimed is:

1. A compound having the structure (I)

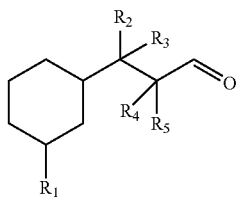

wherein:
$R_1$ is $C_1$ to $C_5$ alkyl; and,
$R_2$ to $R_5$ are independently selected from H and methyl,
and further wherein, when $R_2$ to $R_5$ are each H then $R_1$ is not methyl, wherein the compound possesses a Muguet (Lily-of-the-Valley) odor.

2. A compound according to claim 1, wherein:
$R_1$ is selected from isopropyl, tert-butyl, sec-butyl, isobutyl, 2,2-dimethylpropyl.

3. A compound according to claim 1, wherein at least one of $R_2$ and $R_3$ is H and at least one of $R_4$ and $R_5$ is H.

4. A compound according to claim 1 wherein $R_1$ is tert-butyl and $R_2$ to $R_5$ are each H.

5. A perfumed product comprising a compound according to claim 1.

6. A method of perfuming a product, comprising the step of:
incorporating a compound according to claim 1 in said product.

7. A perfume according to claim 1, wherein the perfume possesses a Muguet (Lily-of-the-Valley) odor.

8. A perfume comprising a compound having the structure (I)

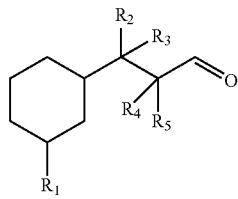

wherein:
$R_1$ to $C_1$ to $C_5$ alkyl; and,
$R_2$ to $R_5$ are independently selected from H and methyl.

9. A perfume according to claim 8, wherein:
$R_1$ is selected from isopropyl, tert-butyl, sec-butyl, isobutyl, 2,2-dimethylpropyl.

10. A perfume according to claim 8, wherein:
at least one of $R_2$ and $R_3$ is H and at least one of $R_4$ and $R_5$ is H.

11. A perfume according to claim 8 wherein:
$R_1$ is tert-butyl and $R_2$ to $R_5$ are each H.

12. A perfume according to claim 8, wherein the compound is present in an amount of at least 0.01% by weight.

13. A perfume according to claim 12, wherein the compound is present in an amount of in the range of from 0.1 to 80% by weight.

14. A perfumed product comprising a perfume according to claim 8.

15. A method of perfuming a product, comprising the step of:
incorporating a perfume according to claim 8 in said product.

* * * * *